(12) United States Patent
Maggi et al.

(10) Patent No.: US 8,047,059 B2
(45) Date of Patent: Nov. 1, 2011

(54) VISCOMETER WITH INTEGRAL SAMPLE RETENTION RESERVOIR

(75) Inventors: Charles Patrick Maggi, State College, PA (US); Brian James Poillucci, State College, PA (US); Keith Graham Carr, Pennsylvania Furnace, PA (US); Frank L. Carbalan, Boalsburg, PA (US)

(73) Assignee: Cannon Instrument Company, State College, PA (US)

( * ) Notice: Subject to any disclaimer, the term of this patent is extended or adjusted under 35 U.S.C. 154(b) by 536 days.

(21) Appl. No.: 12/283,177

(22) Filed: Sep. 10, 2008

(65) Prior Publication Data

US 2010/0058839 A1   Mar. 11, 2010

(51) Int. Cl.
*G01N 11/06* (2006.01)
(52) U.S. Cl. .......... 73/54.07
(58) Field of Classification Search ............. None
See application file for complete search history.

(56) References Cited

U.S. PATENT DOCUMENTS

| | | | |
|---|---|---|---|
| 2,048,305 A | 7/1936 | Ubbelohde | |
| 2,076,591 A * | 4/1937 | Rhodes et al. | 73/54.07 |
| 2,095,282 A | 10/1937 | Payne | |
| 2,095,324 A | 10/1937 | Fitzsimons | |
| 2,343,061 A | 2/1944 | Irany | |
| 2,805,570 A | 9/1957 | Cannon | |
| 3,277,694 A * | 10/1966 | Cannon et al. | 73/54.07 |
| 3,434,338 A | 3/1969 | Tovrog et al. | |
| 3,540,264 A * | 11/1970 | Cerutti et al. | 73/54.04 |
| 3,559,463 A | 2/1971 | Tovrog et al. | |
| 3,798,960 A | 3/1974 | Glass | |
| 3,981,182 A | 9/1976 | Kossler et al. | |
| 4,028,929 A | 6/1977 | Bohm | |
| 4,079,859 A * | 3/1978 | Jennings | 222/1 |
| 4,583,395 A | 4/1986 | Anantaraman | |
| 4,616,503 A * | 10/1986 | Plungis et al. | 73/54.08 |
| 4,685,328 A | 8/1987 | Huebner et al. | |
| 7,111,499 B2 * | 9/2006 | Keen | 73/54.04 |

* cited by examiner

*Primary Examiner* — Hezron E Williams
*Assistant Examiner* — Alex Devito
(74) *Attorney, Agent, or Firm* — Drinker Biddle & Reath LLP (57) ABSTRACT

A viscometer having a substantially horizontal reservoir including a trap for retaining a sample indefinitely in the reservoir. A substantially vertical measuring tube disposed perpendicularly to the substantially horizontal reservoir and depends substantially upwardly from the reservoir. A junction interconnects the trap, a generally downwardly projecting fill tube, and a generally upwardly projecting vent tube.

26 Claims, 6 Drawing Sheets

VISCOMETER WITH INTEGRAL SAMPLE RETENTION RESERVOIR

BACKGROUND OF INVENTION

Glass capillary viscometers of many sizes and configurations are known in the art, including three basic types—suspended level, reverse flow, and Ostwald-style. Perhaps the most commonly used viscometers are the Ubbelohde viscometer (suspended level) and the Cannon-Fenske Routine (Ostwald-style) viscometer. Such viscometers typically comprise a generally U-shaped tube having a first branch tube with a capillary tube of a precise narrow diameter and a second branch tube having a reservoir or bulb for holding a sample of a fluid whose viscosity is to be measured. The tops of the U-shape of these viscometers permit the devices to be immersed and maintained in a closed-bottom bath of liquid which is thermostatically controlled, while allowing the sample to be manipulated under pressure or vacuum or allowed to free-flow under the influence of gravity in the viscometer. The reservoir enables a sample to be held for repeat testing and allows for accurate temperature control and stabilization of the sample prior to testing or in between multiple tests. The capillary tube includes one or more timing bulbs which define the operational range of the viscometer. An upper timing mark or sensor is located above the timing bulb, and a lower timing mark or sensor is located below the timing bulb. A known volume is contained within the first branch tube between the upper and lower timing marks or sensors. The kinematic viscosity can be determined by measuring the time for the fluid to pass between the two timing marks or sensors and multiplying the measured time by a calibration factor that is dependent on various physical dimensions of the viscometer. In a U-shaped viscometer such as a Ubbelohde or Ostwald-style, a fluid sample must typically be added to the second branch tube and held in the reservoir, which presents difficulties for mechanized sample loading in automated viscometers.

A fourth type of viscometer, an Atlantic viscometer, is a straight tube that breaches both the top and bottom of a thermostatically controlled bath of liquid and can be loaded from the bottom by either suction or pressure. However, an Atlantic tube comprises only the components of the first branch tube of an Ostwald-style viscometer, i.e., the timing bulb, upper and lower timing marks or sensors, and capillary tube. Because an Atlantic tube does not contain a reservoir, the same fluid sample cannot be retained in the tube for repeat testing to improve accuracy or for extended periods of thermal soaking prior to testing.

SUMMARY OF INVENTION

An improved viscometer is provided which, in one embodiment, includes a substantially horizontal reservoir with a trap for retaining a sample in the reservoir; a substantially vertical measuring tube depending substantially upwardly from the reservoir; and a junction for interconnecting the trap, a generally downwardly projecting fill tube, and a generally upwardly projecting vent tube. The improved viscometer can be fitted in a thermostatically controlled liquid bath in a similar manner to that of an Atlantic viscometer.

In another embodiment, a viscometer is provided which includes a substantially horizontal reservoir comprising a trap at one end for retaining a sample in the reservoir. The trap has a low point for retaining a predetermined sample volume in the reservoir. A substantially vertical measuring tube extends substantially upwardly from the reservoir and is disposed substantially perpendicularly thereto. The measuring tube includes a timing bulb, an upper timing sensor disposed above the timing bulb, a lower timing sensor disposed below the timing bulb, and a capillary tube located below the lower timing sensor. The capillary tube connects to the reservoir at an opposite end from the trap. A junction interconnects the trap, a generally downwardly projecting fill tube, and a generally upwardly projecting vent tube. The junction has a peak located at least slightly vertically above the trap low point to prevent siphoning of the sample.

Other objects, advantages, and features of the present invention will become apparent to those skilled in the art upon reading the following detailed description, when considered in conjunction with the appended claims and the accompanying drawings briefly described below.

BRIEF DESCRIPTION OF DRAWINGS

The accompanying drawings, which are incorporated herein and constitute a part of this specification, illustrate preferred embodiments of the invention, and together with the general description given above and the detailed description given below, serve to explain features of the invention. However, it should be understood that this invention is not limited to the precise arrangements and instrumentalities shown in the drawings.

DETAILED DESCRIPTION OF THE ILLUSTRATED EMBODIMENTS

Figure 1:
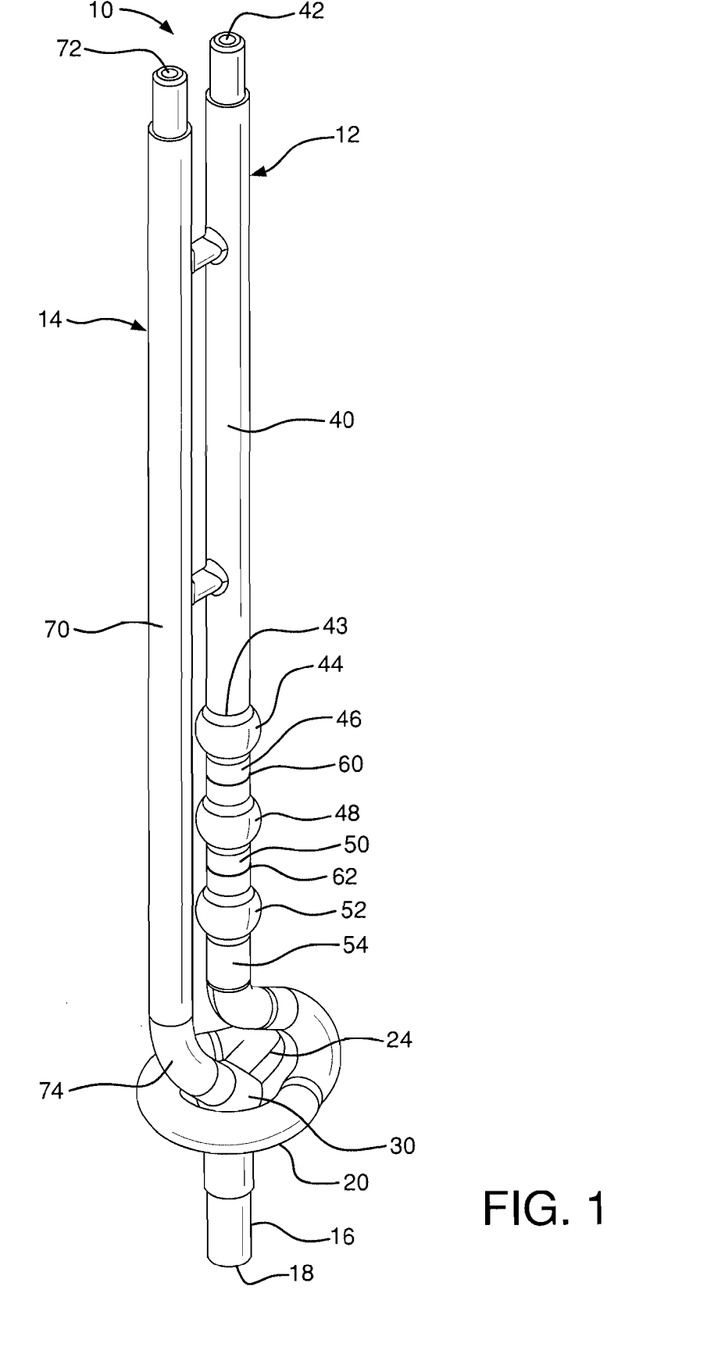
FIG. 1 is a perspective view showing an embodiment of a viscometer.
Figure 2:
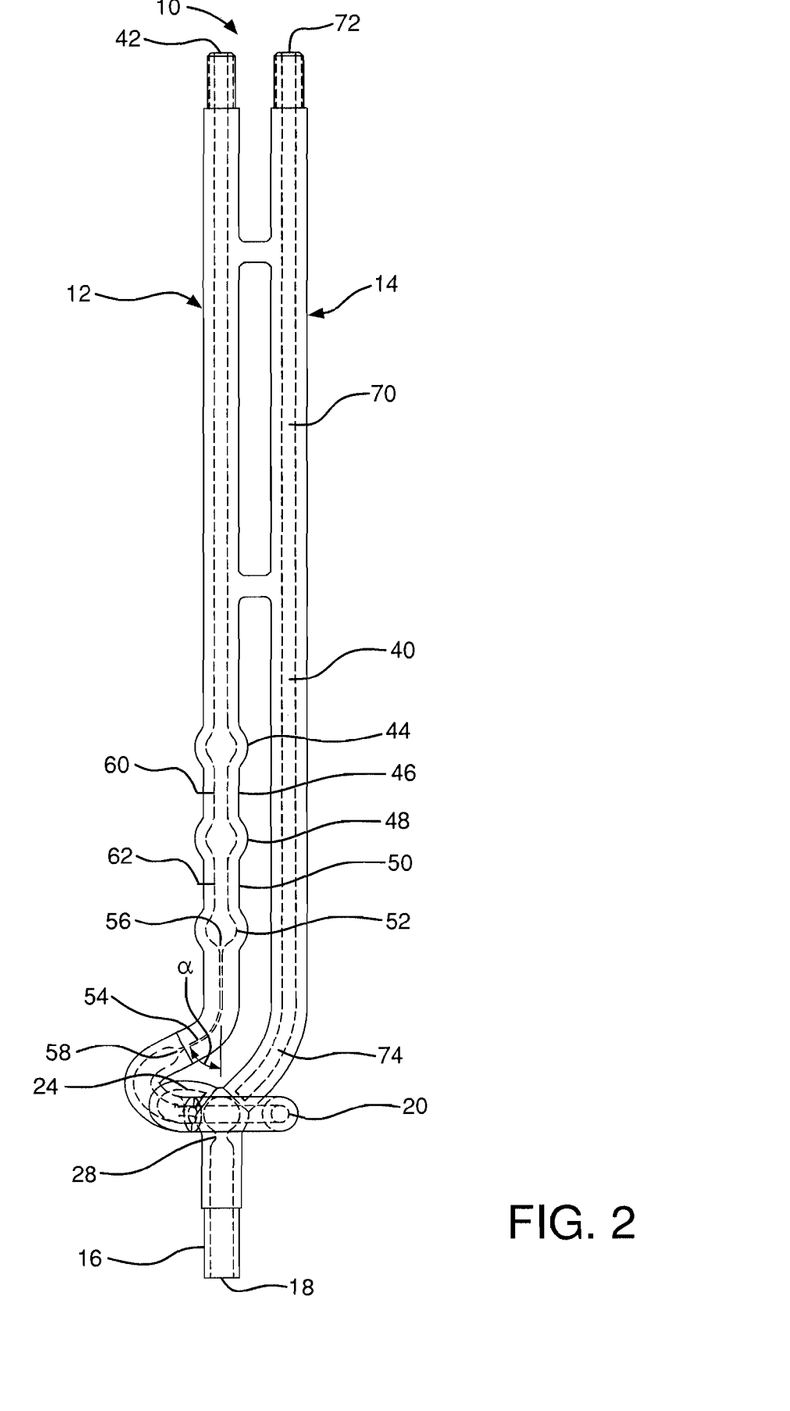
FIG. 2 is a front view showing the viscometer of FIG. 1.
Figure 6:
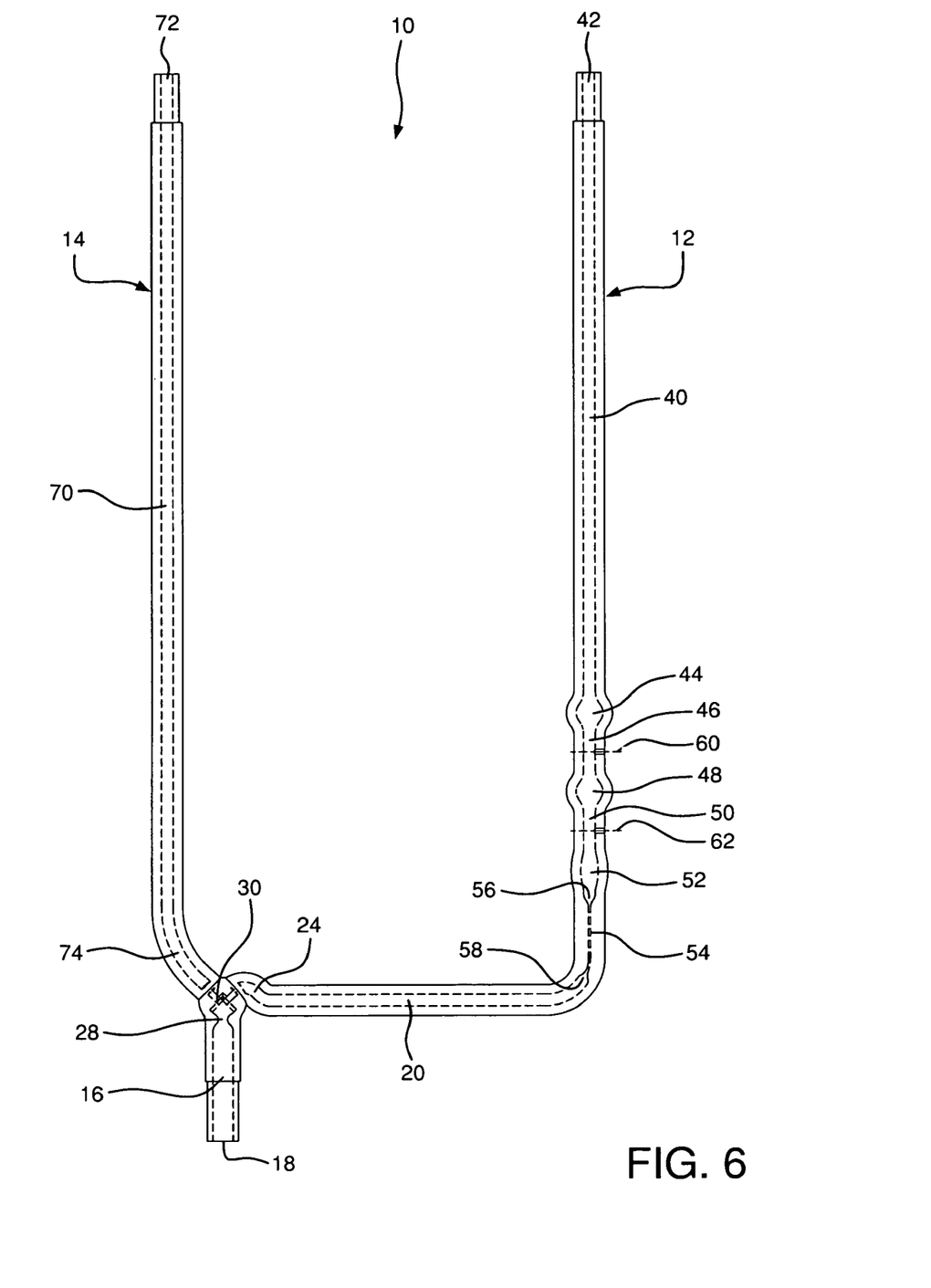
FIG. 6 is a front view of another embodiment of the viscometer according to the present invention.

There is shown in FIGS. 1 and 2 a viscometer 10 comprising a vent tube 14, a fill tube 16, and a measuring tube 12 comprising a reservoir 20. The reservoir 20, the vent tube 14, and the fill tube 16 are interconnected together at a junction 30 so that fluid can pass therebetween. As depicted in the embodiment of FIGS. 1 and 2, the reservoir 20 depends outwardly from the junction 30 in a substantially horizontal orientation and is preferably wrapped generally around a portion of one or both of the junction 30 and the fill tube 16 so as to form a partial ring or helical shape. As depicted in the embodiment of FIG. 6, the reservoir 20 extends outwardly in a substantially straight horizontal orientation and is disposed generally in the same plane as the measuring tube 12, the vent tube 14, and the fill tube 16. In either embodiment, the reservoir 20 is preferably substantially perpendicular to the measuring tube 12. The viscometer 10 can be made of borosilicate glass. Alternatively, the viscometer 10 can be made of other materials such as quartz, plastic, or metal.

The vent tube 14 comprises a tubular body 70 that extends generally upwardly from a transition tube or end 74 adjacent to the junction 30 to an opposite open top end 72. The open end 72 of the vent tube body 70 is adapted to be repeatedly sealed and unsealed, or to be connected to a valve mechanism for automated sealing and unsealing the end 72.

The fill tube 16 extends generally downwardly from the junction 30 to an open bottom end 18. The inside diameter of the fill tube 16 preferably includes a choke 28 or narrow diameter section near where the fill tube 16 connects to the junction 30. The open end 18 of the fill tube 16 is adapted to be connected to or placed within a source of fluid to be tested, such as a fluid container or sample vial. During use, the fluid being tested is drawn up the fill tube 16 into the viscometer 10. In the embodiments of FIGS. 1, 2, 6, and 7, fluid can be aspirated into the viscometer by suction applied at end 42. Alternatively, fluid can be forced upwardly into the viscometer by applying pressure on the fluid container.

The measuring tube 12 includes a tubular body 40 that extends upwardly in a substantially vertical direction from the reservoir 20 to an open top end 42. The measuring tube 12 is preferably substantially perpendicular to the reservoir 20. The end 42 is adapted to be connected to a source of vacuum for drawing fluid into the viscometer 10 and for drawing a sample of fluid from the reservoir 20 upward toward the tubular body 40. An opposed bottom end 43 of the tubular body 40 connects to the top of an overflow bulb 44 into which a sample of fluid can be drawn for viscosity measurement. A first or upper transition tube 46 interconnects the bottom of the overflow bulb 44 to the top of a timing bulb 48 through which a sample is allowed to drain by gravitational force during a measurement time period during which the viscosity of the sample can be determined. The timing bulb 48 has a known fixed volume. In one embodiment, a second or lower transition tube 50 interconnects the bottom of the timing bulb 48 to the top of a capillary tube 54, and the bottom of the capillary tube 54 opens onto the reservoir 20. In another embodiment, a small runout bulb 52 is interposed between the bottom of the timing bulb 48 and the top of the capillary tube 54. The run out bulb 52 is a convenient way to adjust the volume contained in the vertical measuring tube 12, during manufacturing, to match the volume contained in the horizontal reservoir 20 up to the trap 24. The capillary tube 54 has a known diameter and a known length. The height difference between the timing bulb 48 and the top of the capillary tube 54 is also known.

When a fluid sample is in the measuring tube 12, it is readily understood by a person having ordinary skill in the relevant art that the sample forms a column of fluid having a top meniscus and a bottom meniscus, due to the interaction between the adherence of the fluid to the tube walls and the surface tension of the fluid itself. As the fluid flows generally downward under the influence of gravity, the bottom meniscus is termed the leading meniscus and the top meniscus is termed the trailing meniscus. Preferably, the leading meniscus and the trailing meniscus have approximately the same diameter such that the effects of surface tension on the viscometer measurement can be eliminated. This is in contrast to other designs. For example, in suspended-level viscometers (e.g., the Ubbelohde viscometer), the trailing meniscus has a diameter about twice as large as that of the leading meniscus (which is located just at the exit of the capillary). For another example, in Ostwald-style viscometers, the leading meniscus (contained in a large diameter reservoir) is more than ten times as large in diameter than the trailing meniscus.

An upper timing sensor 60 is preferably located in the first transition tube 46 above the timing bulb 48 and detects the passage of the fluid sample as gravity pulls the sample downward through the measuring tube 12 from the overflow bulb 44 to the timing bulb 48 in a conventional manner. A lower timing sensor 62 is preferably located in the second transition tube 50 below the timing bulb 48 and detects the passage of the fluid sample as gravity pulls the sample downward from the timing bulb towards the capillary tube 54. The capillary tube 54 regulates the rate of passage of a fluid sample through the measuring tube 12 such that, based on the diameter and length of the capillary tube 54, the volume of the timing bulb 48, and the height of the fluid column above the capillary tube 54 (i.e., the hydrostatic head forcing the fluid through the capillary tube 54), the time of passage of the fluid sample through the timing bulb 48 (i.e., between the upper sensor 60 and the lower sensor 62) can be correlated with the kinematic viscosity of the sample using Poiseulle's Law.

The reservoir 20 holds a predetermined sample volume, i.e., a sufficiently large volume of fluid such that all of the elements above the capillary tube 54, up to and including a portion of the overflow bulb 46, remain filled until after the leading meniscus of the fluid under test enters the horizontal portion of the reservoir 20. This ensures a consistent driving head for the sample during the entire measurement time period during which the trailing meniscus of the sample (i.e., the fluid level) is falling between the sensor 60 and the sensor 62. Thus, the predetermined sample volume is preferably defined as at least the volume contained in the measuring tube 12 from the upper sensor 60, through the bottom of the capillary tube 54, and just into the horizontal reservoir 20, i.e., sum of the volume which passes between the two sensors 60 and 62 when the sample is gravitationally drained as regulated by the capillary tube 54 plus the volume required to make sure the capillary tube 54 is fully wetted throughout the measurement time period when the trailing meniscus is passing between the two sensors 60 and 62.

The kinematic viscosity of a Newtonian or mildly non-Newtonian fluid can be measured using an embodiment of a viscometer 10 as disclosed herein. An exemplary sequence of operation is as follows, with particular reference to the embodiment of FIGS. 1 and 2. Similar sequences of operation are readily apparent to one skilled in the art with regard to various other embodiments, including that shown in FIG. 6.

The viscometer 10 is placed into a holder or other fixturing mechanism for holding the viscometer 10 steady while viscosity determinations (e.g., calibrations or measurements) are being made. The holder can be loaded or mounted within a conventional viscometer testing apparatus, which is capable of accurately controlling the temperature environment within which the viscometer 10 is located, thus controlling the temperature of the fluid contained within the viscometer 10. Accurate temperature control increases the accuracy and repeatability of kinematic viscosity measurements. Although temperature control, per se, is beyond the scope of the viscometer 10 acting alone, a viscometer 10 adapted to contain a predetermined sample volume that can be repeatedly tested without reloading a new sample facilitates consistency of temperature control. Furthermore, many industries require that kinematic viscosity testing occur at a precise temperature, and/or require an extended thermal "soak" (i.e., holding a viscosity sample at a predetermined temperature for an extended period of time.) Thus, being able to maintain the fluid sample in the reservoir for an indefinite time period in a thermostatically controlled bath (liquid or air) is desirable. Also, the viscometer 10 itself precisely regulates the volume of sample being measured, since the volume of the reservoir 20 defines the sample volume and is independent of the temperature at which the sample is soaked.

The open end 18 of the fill tube 16 is exposed to a source of fluid from which a sample will be obtained (e.g., a fluid container). The top end 72 of the vent tube 14 is sealed and vacuum is applied to the measuring tube 12 via the top end 42 such that fluid is drawn up through the open end 18 of the fill tube, through the junction 30, over the trap 24, and into the reservoir 20. Vacuum is preferably maintained on the end 42 of the measuring tube 12 fluid until the reservoir 20 is filled and fluid moves up to timing mark 60. The sample is then allowed to drain back down into the reservoir 20 where it remains indefinitely for purposes of thermal soaking or until such time that a test measurement is desired. Note that an alternative method for filling the reservoir 20 includes applying pressure to the sample container while opening the end 42 of the measuring tube 12 to atmosphere.

One indicator of a full reservoir 20 is that the fluid is drawn up into at least a portion of the capillary tube 54 before the vacuum or pressure is released. Another indicator of a full reservoir 20 is that the entire horizontal portion of the measuring tube 12 between the trap 24 and the capillary tube 54 is full. Yet another indicator of a full reservoir 20 is that the fluid level in the reservoir 20 is at or above the level of a low point 26 in the trap 24.

Next, the end 72 of the vent tube 14 is unsealed and allowed to be exposed to ambient (i.e., atmospheric) pressure, enabling fluid to drain from the junction 30 and the fill tube 16. Vacuum is removed from the end 42 of the measuring tube 12 and exposed to ambient pressure, enabling the fluid level in the reservoir 20 to stabilize to a predetermined volume. The predetermined volume is greater than or equal to the amount of fluid required to fill the measuring tube from just below the capillary tube 54 to just above the upper sensor 60 and partially into the overflow bulb 44, which is the minimum sample volume required for an accurate viscosity measurement.

Figure 3:
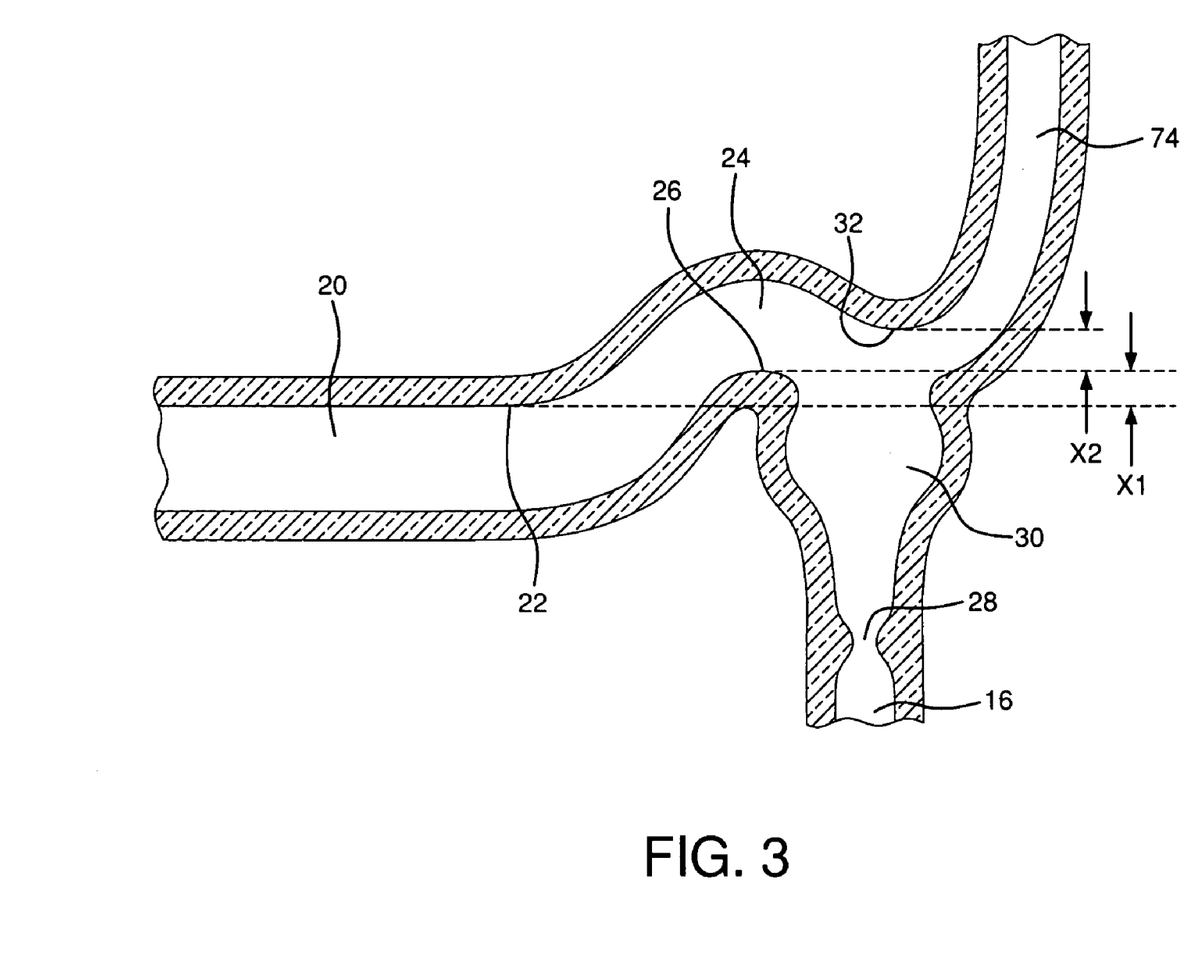
FIG. 3 is an expanded cross-sectional view of a trap in one embodiment of the viscometer.

When vacuum is removed from the end 42 of the measuring tube 12, the fluid in the reservoir 20 is prevented from flowing back down the fill tube 16 for one or more of the following reasons. As illustrated in the embodiment of FIG. 3, the trap 24 has a low point 26 that is aligned with or slightly above the vertical location of a top 22 of the reservoir (i.e., the dimension X1 is greater than or equal to zero). In a substantially horizontal reservoir 20, as shown in the embodiment of FIGS. 1-2, the top 22 can be the highest point on the inside wall of the reservoir 20. A similar arrangement applies for the embodiment of FIG. 6.

Returning to the embodiment of FIGS. 1-3, fluid is further prevented from being siphoned out of the reservoir 20 by the presence of an air break in conjunction with the choke 28 in the fill tube 16 that slows the downward flow of fluid from the junction 30 As shown in FIG. 3, the junction 30 has a peak 32 where the transition end 74 of the vent tube 70 joins the junction 30. The peak 32 is located at a vertical level that is at least slightly above the height of the trap low point 26 (i.e., the dimension X2 is greater than zero), such that as fluid flows out of the reservoir 20 over the trap 24, air is enabled to enter to upper portion of the trap 24 to disrupt any siphoning effect that could otherwise occur, while still allowing fluid to flow out of the trap 24 with the trap low point 26 acting as a weir. The maximum volume of fluid in the reservoir 20 is set based on the internal volume of the reservoir 20 up to the height of the trap low point 26. Additionally, the reservoir 20 can serve as a holding chamber for indefinite thermal soaking of a sample, as required by certain sample types, and to ensure consistency of measurements.

After the reservoir 20 is filled with a fluid sample, the sample can be repeatedly raised above the timing bulb 48 and its efflux time measured as it falls back to the reservoir 20 under the influence of gravity. The test can be repeated using the same sample as many times as desired to quantify its behavior, and the results averaged if desired, to obtain a consistent viscosity value. Because the same sample is reused each time, there is no need for thermal stabilization between measurements. To determine the viscosity of a sample, vacuum is applied to the end 42 of the measuring tube 12 to draw a column of the fluid sample upward toward the tubular body 40. Alternatively, pressure is applied to the sample vial while the end 42 is open to atmosphere to aspirate a sample. The sample is drawn through the capillary tube 54, through the runout bulb 52 (if present), past the lower sensor 62, and into the timing bulb 48 to a level that rises above the upper sensor 60. The sample can be drawn further upward into the overflow bulb 44 and even into the tubular body 40, although it is not necessary for viscosity measurement to draw the sample significantly above the upper sensor 60.

The timing sensors 60 and 62 can be mere indicator lines marked or etched onto the measuring tube 12, or they can be electrical sensors, thermal sensors, optical sensors, or another type of sensor that can equivalently sense the difference between fluid and air space so as to determine the passage of the meniscus of a falling column of fluid in the tube 12. The sensors 60 and 62 preferably have a response time equal to or less than 10 ms, as well as limited measurement hysteresis. In one embodiment, the sensors 60 and 62 are infrared optical sensors. In another embodiment, the sensors 60 and 62 are through-mounted NTC thermistors.

Once the fluid has been drawn above the upper sensor 60, the end 42 of the tube 12 is released from vacuum. Ambient air pressure is allowed to contact the trailing meniscus (i.e., top surface) of the fluid column, causing the fluid column to fall through the measuring tube 12 under the force of gravity. The driving force pushing the fluid through the capillary tube 54 is merely the static head resulting from the height of the fluid column in the measuring tube 12, i.e., the height of the liquid column above the top of the capillary tube 54. As the fluid falls, the upper sensor 60 detects the passage of the trailing meniscus. If the upper sensor 60 is a mark on the measuring tube 12, detection comprises a user observing the meniscus crossing or falling below the mark and starting a timer or recording a start time. If the sensor 60 is an electronic or optical sensor, a timer is automatically started or a start time is automatically recorded. As the fluid exits the timing bulb 48 and crosses or falls below the lower sensor 62, the lower sensor 62 detects the passage of the trailing meniscus as a trigger point at which timing is stopped. If the lower sensor 62 is a mark on the measuring tube 12, detection comprises a user observing the meniscus falling below the mark and stopping the timer or recording a stop time. If the sensor 62 is an electronic or optical sensor, the timer is automatically stopped or a stop time is automatically recorded. The sample efflux time is then recorded or stored electronically as the elapsed time between the trailing meniscus crossing the two timing marks 60 and 62.

The rate of fluid returning to the reservoir 20 is regulated by the internal cross-sectional diameter of capillary tube 54 according to Poiseulle's Law. Therefore, different diameters of capillary tubes can be used to measure fluids of different kinematic viscosity ranges, in order to obtain reasonably measurable periods of time between the sensors 60 and 62 where the timing resolution is a small percentage of the overall sample efflux time and the imparted kinetic energy is small. It is noted that the viscometer 10 can be equipped with any number of timing bulbs 48 disposed serially along the measuring tube 12, each timing bulb 48 having an associated upper sensor 60 and lower sensor 62. Each timing bulb 48 would have a different sample volume such that fluids in different viscosity ranges can be tested in the same viscometer 10. For example, a first timing bulb 48 can have a volume 10 times as large as the volume of a second timing bulb 48, such that a first fluid having a first viscosity can be tested using the first timing bulb 48 and a second fluid having a second viscosity one order of magnitude greater can be tested using the second timing bulb 48.

Figure 4:
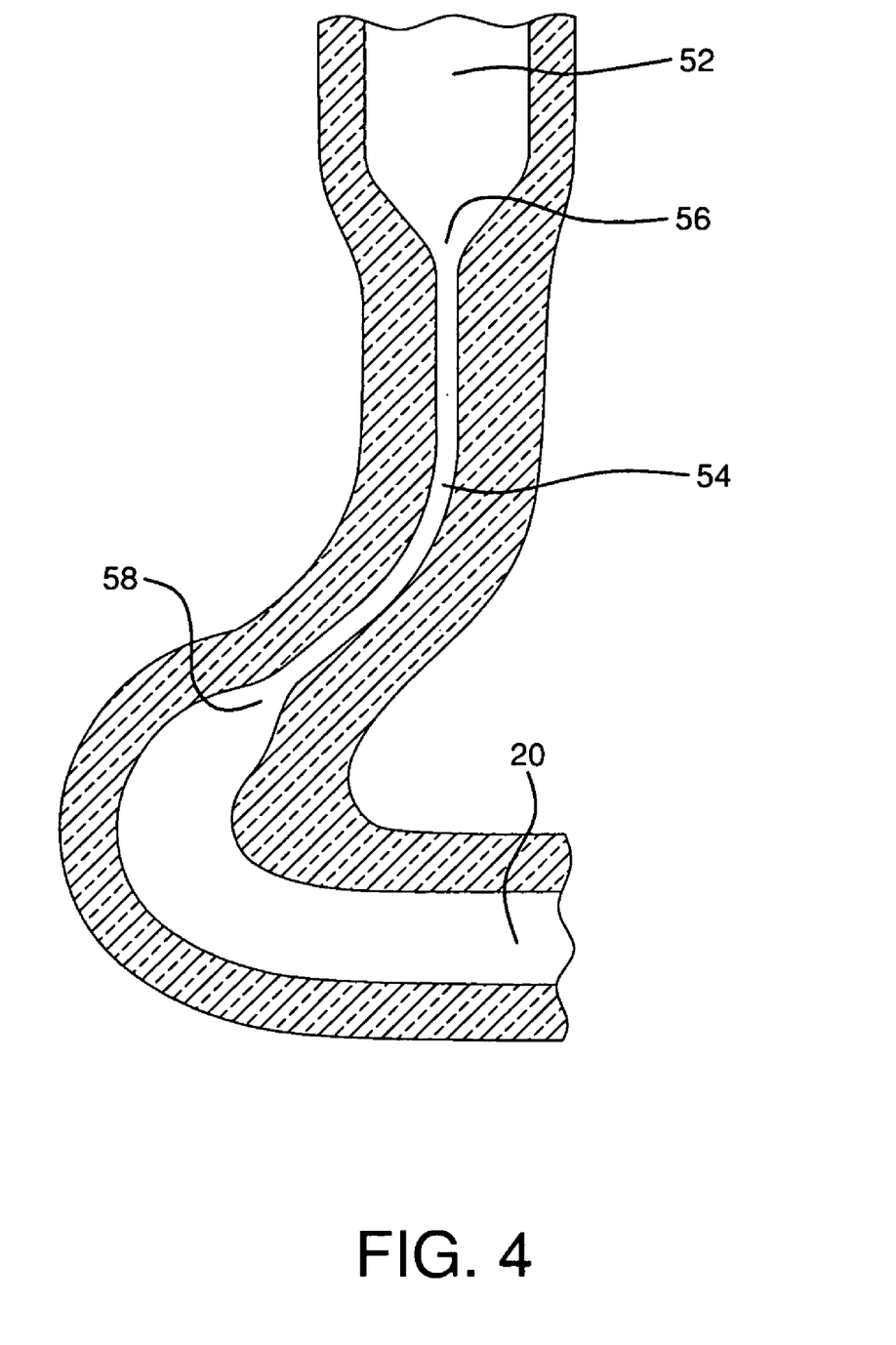
FIG. 4 is an enlarged partial front view showing a capillary tube formed in the viscometer.
Figure 5:
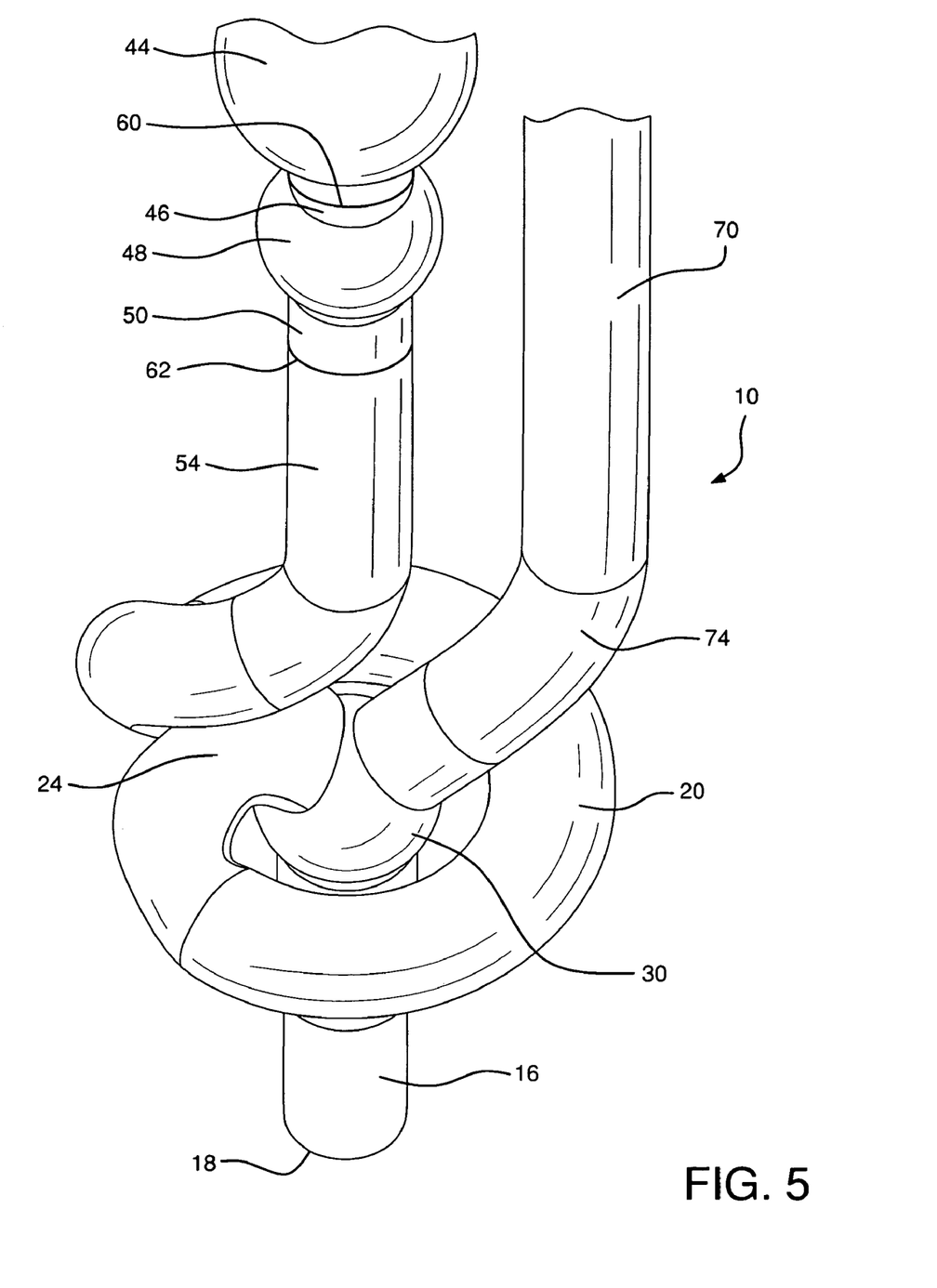
FIG. 5 is an enlarged perspective view showing a portion of the viscometer of FIG. 1.

The geometry of the capillary tube 54 can influence the accuracy and repeatability of viscosity measurements. As shown in detail FIG. 4, the capillary tube 54 has an upper transition portion 56 and a lower transition portion 58. As the column of fluid flows downward in the measuring tube 12, the upper transition portion 56 is at the inlet of the capillary tube 54 and the lower transition portion 58 is at the outlet of the capillary tube 54. In one embodiment, the upper and lower transition portions 56 and 58 have substantially similar shapes. For example, the transition portions 56 and 58 can have trumpeted shapes. The use of similar shaped inlet and outlet shapes provides for uniform energy dissipation as a result of the fluid being forced into a small capillary constriction from a relatively large diameter tube and then back again into a relatively large diameter tube. In another embodiment, the lower transition portion 58 is shaped so as to result in nearly complete energy dissipation at the outlet of the capillary tube 54 to improve the precision of measurements and to reduce the need to correct measured times for the effects of kinetic energy of the fluid exiting the capillary tube 54, which tends to draw or accelerate the sample through the capillary tube 54 more quickly. A kinetic energy correction may particularly be required for fluids in which measured sample flow times are less than about 200 seconds for samples of low kinematic viscosity. The shape of the lower transition portion 58 can include both the gradual expansion of the internal diameter of the tube and the offset of the lower transition portion 58 from vertical by an angle. The angle of offset from vertical is preferably between about 30 degrees and about 60 degrees and is more preferably about 45 degrees to facilitate smooth transition to the horizontal reservoir 20, but may vary from 0 degrees to no more than 90 degrees.

While the invention has been disclosed with reference to certain preferred embodiments, numerous modifications, alterations, and changes to the described embodiments are possible without departing from the sphere and scope of the invention, as defined in the appended claims and equivalents thereof. Accordingly, it is intended that the invention not be limited to the described embodiments, but that it have the full scope defined by the language of the following claims.

We claim:

1. A viscometer comprising:
    a substantially horizontal reservoir including a trap for retaining a sample in the reservoir;
    a substantially vertical measuring tube extending substantially upwardly from the reservoir, the arrangement of the measuring tube adapted to permit a fluid to be drawn up into the tube from the reservoir for measuring and returned to the reservoir after measuring thereby permitting repeated measurements of the same fluid;
    said measuring tube also comprising a capillary tube;
    a generally downwardly projecting fill tube;
    a generally upwardly projecting vent tube; and
    a junction interconnecting the trap, the fill tube and the vent tube, the fill tube extending downward from the junction with an open end of the fill tube located below the junction, and the vent tube extending upward from the junction with an open end positioned above the junction.

2. The viscometer of claim 1, wherein the trap has a low point that is slightly above the vertical location of the top of the reservoir for retaining a predetermined sample volume in the reservoir.

3. The viscometer of claim 2, wherein the junction has a peak where the vent tube joins the junction that is located at least slightly vertically above the trap low point for preventing siphoning of the sample from the reservoir.

4. A viscometer comprising:
    a substantially horizontal reservoir including a trap for retaining a sample in the reservoir;
    a substantially vertical measuring tube extending substantially upwardly from the reservoir;
    a generally downwardly projecting fill tube;
    a generally upwardly projecting vent tube;
    a junction interconnecting the trap, the fill tube and the vent tube;
    wherein the trap has a low point for retaining a predetermined sample volume in the reservoir, the junction has a peak disposed at least slightly vertically above the trap low point for preventing siphoning of the sample from the reservoir; and
    the fill tube further comprising a choke disposed therein near the junction for further preventing siphoning of the sample from the reservoir.

5. The viscometer of claim 1, wherein the reservoir is disposed substantially perpendicularly to the vertical measuring tube.

6. The viscometer of claim 5, wherein the reservoir is substantially coplanar with the measuring tube, the fill tube, and the vent tube.

7. A viscometer comprising:
    a substantially horizontal reservoir including a trap for retaining a sample in the reservoir;
    a substantially vertical measuring tube extending substantially upwardly from the reservoir;
    a generally downwardly projecting fill tube;
    a generally upwardly projecting vent tube; and
    a junction interconnecting the trap, the fill tube and the vent tube;
    wherein the reservoir is disposed substantially perpendicularly to the vertical measuring tube, and
    wherein the reservoir is wrapped about one or both of the junction and the fill tube so as to form a partial ring.

8. The viscometer of claim 1, the measuring tube comprising a timing bulb, an upper timing sensor disposed above the timing bulb, a lower timing sensor disposed below the timing bulb, and a capillary disposed below the lower timing sensor, the capillary interconnecting between the timing bulb and the reservoir.

9. The viscometer of claim 8, further comprising a runout bulb disposed between the timing bulb and the capillary.

10. The viscometer of claim 1, the measuring tube comprising two or more timing bulbs, an upper timing sensor disposed above each timing bulb, a lower timing sensor disposed below each timing bulb, and a capillary disposed below the timing bulbs and sensors, the capillary interconnecting between the timing bulbs and the reservoir.

11. The viscometer of claim 8, the capillary tube having an upper transition section and a lower transition section, the upper transition section and the lower transition section having substantially similar shapes.

12. The viscometer of claim 11, wherein the upper transition section of the capillary tube is disposed substantially vertically and the lower transition section of the capillary tube is disposed at an angle less than 90 degrees and greater than 0 degrees from vertical.

13. The viscometer of claim 12, wherein the lower transition section of the capillary tube is disposed at an angle from vertical of about 45 degrees.

14. The viscometer of claim 8, wherein each timing sensor comprises an etched timing line for detecting the passage of a meniscus of a sample.

15. The viscometer of claim 8, wherein each timing sensor comprises a thermistor for detecting the passage of the meniscus of a sample.

16. The viscometer of claim 8, wherein each timing sensor comprises an optical sensor for detecting the passage of the meniscus of a sample.

17. The viscometer of claim 1, wherein one end of the fill tube opens onto the junction and an opposed end of the fill tube is adapted to be connected to a source of fluid to be drawn into the reservoir; wherein one end of the vent tube opens onto the junction and an opposed end of the vent tube is adapted to be repeatedly sealed and unsealed; and wherein one end of the measuring tube opens onto the reservoir and an opposed end of the measuring tube is adapted to connected to a source of vacuum.

18. The viscometer of claim 17, further comprising a J-tube connected to the opposed end of the fill tube for enabling filling of the viscometer from above.

19. A viscometer comprising:
a substantially horizontal reservoir including a trap at one end for retaining a sample in the reservoir, the trap having a low point for retaining a predetermined sample volume in the reservoir;
a substantially vertical measuring tube extending substantially upwardly from the reservoir and disposed substantially perpendicularly thereto, the measuring tube comprising a timing bulb, an upper timing sensor disposed above the timing bulb, a lower timing sensor disposed below the timing bulb, and a capillary tube disposed below the lower timing sensor, the capillary tube connecting to the reservoir at an opposite end thereof from the trap;
a downwardly projecting fill tube;
an upwardly projecting vent tube; and
a junction connecting the trap, the fill tube, and the vent tube, the junction having a peak located at a point slightly vertically above the trap low point for preventing siphoning of the sample.

20. The viscometer of claim 19, wherein the reservoir has a partial ring shape extending around a portion of one or both of the junction and the fill tube.

21. The viscometer of claim 19, wherein the reservoir has a substantially straight shape.

22. The viscometer of claim 19, the capillary tube having an upper transition portion and a lower transition portion, the upper and lower transition portion having substantially similar shapes.

23. The viscometer of claim 22, wherein the upper transition portion of the capillary tube is disposed substantially vertically and the lower transition portion of the capillary tube is disposed at an angle of between about 30 degrees and about 60 degrees from vertical.

24. The viscometer of claim 19, wherein each timing sensor comprises an electrical sensor for detecting the passing of a meniscus of a sample.

25. The viscometer of claim 24, wherein the electrical sensor is an infrared optical sensor.

26. The viscometer of claim 19, wherein each timing sensor comprises a thermistor for detecting the passage of a meniscus of a sample.

* * * * *